(12) United States Patent
Guy

(10) Patent No.: US 9,858,657 B2
(45) Date of Patent: Jan. 2, 2018

(54) APPARATUS AND A METHOD OF MACHINING A SHAPE THROUGH A COMPONENT

(71) Applicant: ROLLS-ROYCE plc, London (GB)

(72) Inventor: Graham Charles Guy, Nottingham (GB)

(73) Assignee: ROLLS-ROYCE plc, London (GB)

(*) Notice: Subject to any disclaimer, the term of this patent is extended or adjusted under 35 U.S.C. 154(b) by 36 days.

(21) Appl. No.: 14/996,776

(22) Filed: Jan. 15, 2016

(65) Prior Publication Data

US 2016/0239955 A1    Aug. 18, 2016

(30) Foreign Application Priority Data

Feb. 13, 2015 (GB) .................................. 1502379.9

(51) Int. Cl.
| | |
|---|---|
| *G06T 7/00* | (2017.01) |
| *B23K 26/03* | (2006.01) |
| *B23K 26/14* | (2014.01) |
| *G01N 21/954* | (2006.01) |
| *B23K 26/382* | (2014.01) |
| *B23H 1/04* | (2006.01) |

(Continued)

(52) U.S. Cl.
CPC ............. *G06T 7/0006* (2013.01); *B23H 1/04* (2013.01); *B23K 26/03* (2013.01); *B23K 26/032* (2013.01); *B23K 26/14* (2013.01); *B23K 26/382* (2015.10); *G01N 21/15* (2013.01); *G01N 21/954* (2013.01); *H04N 5/2256* (2013.01); *B23K 2201/001* (2013.01); *B64F 5/10* (2017.01); *G01N 2021/151* (2013.01); *G06T 2207/30164* (2013.01)

(58) Field of Classification Search
None
See application file for complete search history.

(56) References Cited

U.S. PATENT DOCUMENTS

| | | | | |
|---|---|---|---|---|
| 4,027,686 A | * | 6/1977 | Shortes | ............ H01L 21/67051 |
| | | | | 134/102.1 |
| 5,442,155 A | * | 8/1995 | Nihei | ................... B23K 9/0956 |
| | | | | 219/124.34 |

(Continued)

OTHER PUBLICATIONS

Oct. 21, 2015 Search Report issued in British Patent Application No. GB1502379.9.

(Continued)

*Primary Examiner* — Vu Le
*Assistant Examiner* — Tracy Mangialaschi
(74) *Attorney, Agent, or Firm* — Oliff PLC

(57) ABSTRACT

A method of laser drilling a hole comprising providing a laser source at a first side of a component to laser drill a hole through the component. A light source is positioned in the path of the laser beam at the opposite side of the component. A camera is provided at the first side of the component. The camera is positioned such that it has a line of sight view of the light source through the laser drilled hole. The laser drilled hole in the component is viewed using the light provided by the light source at the opposite side of the component. The parameters of the laser drilled hole are measured using the view of the laser drilled hole provided by the camera and a flow of gas is provided over the surface of the light source to protect the light source.

30 Claims, 8 Drawing Sheets

(51) Int. Cl.
*H04N 5/225* (2006.01)
*G01N 21/15* (2006.01)
*B23K 101/00* (2006.01)
*B64F 5/10* (2017.01)

(56) References Cited

U.S. PATENT DOCUMENTS

| | | |
|---|---|---|
| 6,580,054 B1 | 6/2003 | Liu et al. |
| 2005/0095819 A1* | 5/2005 | Liu ................. B23K 26/032 438/464 |
| 2008/0200012 A1* | 8/2008 | Oba ................. B23K 26/03 438/463 |
| 2011/0042362 A1* | 2/2011 | Maehara ........... B23K 26/142 219/121.67 |
| 2011/0120981 A1* | 5/2011 | Paganelli .......... B23K 26/0823 219/121.67 |
| 2012/0092681 A1* | 4/2012 | Cox ................. G01N 21/954 356/626 |
| 2013/0068738 A1 | 3/2013 | Schurmann et al. |
| 2015/0202742 A1* | 7/2015 | Elfizy ............... B24D 5/10 451/56 |

OTHER PUBLICATIONS

Jul. 21, 2016 Extended Search Report issued in European Patent Application No. 16151248.8.

\* cited by examiner

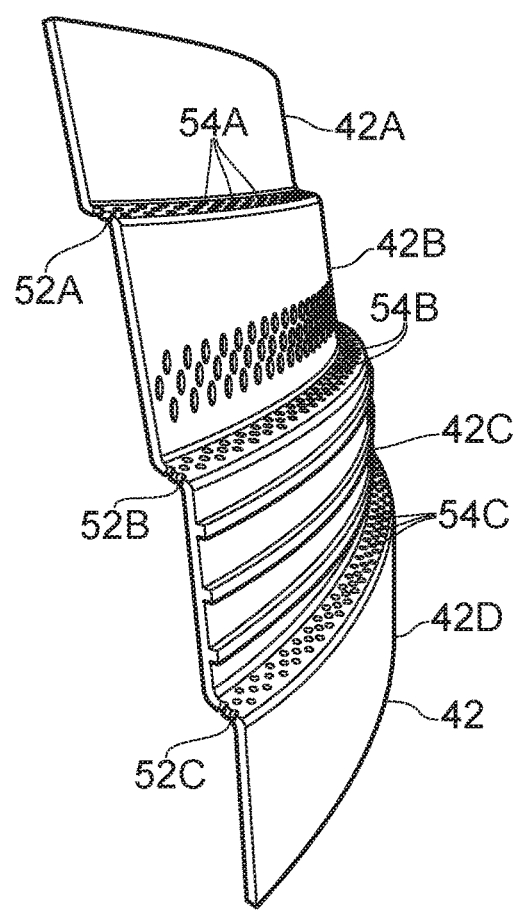
FIG. 3
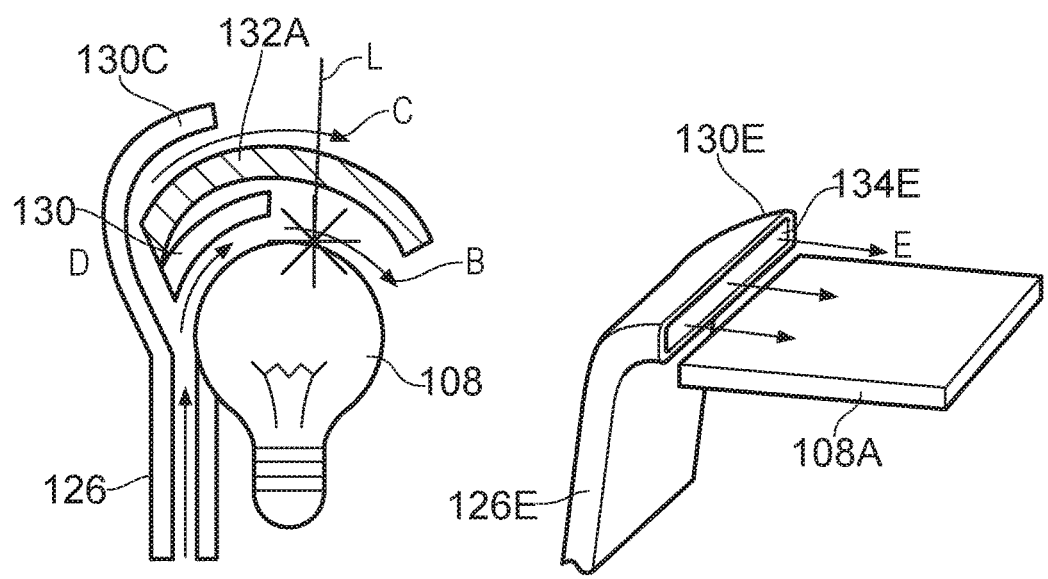
FIG. 8
FIG. 9

APPARATUS AND A METHOD OF MACHINING A SHAPE THROUGH A COMPONENT

FIELD OF THE INVENTION

The present disclosure relates to an apparatus and a method of machining a shape through a component, in particular relates to an apparatus and a method of machining a shape through a gas turbine engine component and more particularly relates to an apparatus and a method of laser drilling a hole through a gas turbine engine component.

BACKGROUND TO THE INVENTION

Currently the most accurate method of visually inspecting laser drilled holes comprises placing a light source at one side of a component through which a hole has been laser drilled and providing a camera at the opposite side of the component. This is known as "backlighting" the hole. Backlighting the hole provides good contrast between the hole and the component and enables the use of edge detection software to determine the edge of the hole in the component. The camera is arranged to view the laser drilled hole and an associated computer with edge detection software determines if the laser drilled hole conforms to the required position, dimensions and shape etc. However, this method of visually inspecting a laser drilled hole is performed "offline" after the hole has been drilled. If the laser drilled hole does not conform to the requirements, it is necessary to re-drill the hole in the component such that it conforms to the requirements.

Conventionally components with a plurality of laser drilled cooling holes are inspected many times during the manufacturing process and this involves stopping the laser drilling process to measure the position, dimensions and shape of the cooling holes to ensure that they conform to the requirements.

There is requirement to inspect the laser drilled holes "online" during the laser drilling process and to correct the laser drilled holes as they are produced via a feedback loop. This would be advantageous because it would avoid the need to stop the laser drilling process for manual inspection, increase productivity, reduce the scrap rate and avoid the need for re-drilling.

In order to inspect the laser drilled holes "online" or "in-process" it is necessary to provide "backlighting" for the camera to view the component because this type of illumination provides the most accurate edge detection for the laser drilled hole.

However, there is a problem if "backlighting" is used to illuminate the component and the laser drilled hole in the component because the light source is in the direct path of the laser beam. The use of "backlighting" has two significant disadvantages. Firstly the dross, dust, spatter, e.g. the molten material droplets and/or molten material droplets which have cooled and solidified, produced by the laser drilling through the component quickly collects on the light source thereby reducing the light output from the light source and hence makes the comparative measurements extremely difficult. Secondly the laser beam directly strikes the light source once it has drilled through the component which heats the light source thereby leading to degradation and eventual failure of the light source.

Therefore the present invention seeks to provide a novel apparatus and method of machining a shape through a component, which reduces or overcomes the above mentioned problem.

SUMMARY OF THE INVENTION

Accordingly the present disclosure provides an apparatus for machining a shape through a component comprises a tool, a light source, a camera and a processor, the light source is positioned in the path of the tool, the camera is positioned or positionable such that it has a line of sight view of the light source through the machined shape through the component, the processor is arranged to measure the parameters of the machined shape through the component using the view of the machined shape provided by the camera, the processor is arranged to compare the measured parameters of the machined shape through the component with required parameters for the machined shape through the component and a device is arranged to provide a flow of fluid over the surface of the light source.

The light source may be a point light source or a diffuse light source.

The light source may be a light bulb, a light emitting diode (LED) or a fluorescent tube. The light bulb may be a tungsten filament bulb, a halogen bulb or an energy saving bulb. The diffuse light source may be a panel comprising a plurality of LEDs or a diffusing reflector and a light source.

The device may comprise a supply nozzle to blow the fluid over, e.g. across, the surface of the light source and/or collector nozzle to suck the fluid over, across, the surface of the light source. The device may comprise a pump to pump the fluid over the surface of the light source. The device may comprise a pump to evacuate the fluid from the surface of the light source. If the fluid is a liquid the surface of the light surface may be arranged at an angle to the horizontal such that the fluid also flows across the surface of the light source under the action of gravity.

The supply nozzle may be positioned adjacent to the light source.

The supply nozzle may have an elongate outlet to provide a sheet of fluid over the light source.

The device may comprise a source of gas. The source of gas may be a source of high pressure gas. The source of gas may be a source of air, a source of nitrogen or a source of an inert gas. The gas may be dried and filtered.

The collector nozzle may be positioned adjacent to the light source.

The collector nozzle may have an elongate inlet to collect a sheet of fluid after it has passed over the surface of the light source.

The collector nozzle and the supply nozzle may be positioned on opposite sides of the light source.

The tool and the camera may be positioned at a first side of the component and the light source is positioned at the opposite side of the component in use and the supply nozzle and/or the collection nozzle are positioned at the opposite side of the component.

The component, the light source and the supply nozzle and/or the collector nozzle may remain in fixed positions relative to each other in use.

A transparent shield may be provided to further protect the light source.

The transparent shield may be sacrificial and/or abradable.

The transparent shield may be provided between the light source and the flow of fluid or the flow of fluid may be provided between the light source and the transparent shield.

The transparent shield may be a sheet of glass or a sheet of polymeric material.

The tool may be a laser source to laser machine a shape through the component.

The camera may be positioned such that it has a permanent line of sight view of the light source through the laser machined shape, an optical switch is provided in the path of the laser beam, the optical switch is switchable between a first position for supplying the laser beam there-through to laser machine the shape through the component and a second position for allowing the camera to view the laser machined shape.

Alternatively the camera may be positioned such that it has a temporarily line of sight view of the light source through the laser machined shape, the camera is movable between a first position in which the camera is not in the optical path of the laser beam to allow the laser beam to laser machine the shape through the component and a second position in which the camera is in the optical path of the laser beam for allowing the camera to view the laser machined shape.

The camera may be mounted on a robotic arm.

The camera may be mounted on the laser source but offset from optical axis of the laser beam, the laser source and the camera are movable together so that the camera is in the optical path used by the laser beam to machine the shape, for allowing the camera to view the laser machined shape.

The laser machined shape may be a laser drilled hole.

If the processor determines that the measured parameters of the laser drilled hole do not satisfy at least one of the required parameters for the laser drilled hole the laser source is arranged to re-drill the laser drilled hole in the component or if the processor determines that the measured parameters of the laser drilled hole satisfy the required parameters of the laser drilled hole the processor is arranged to terminate the laser drilling.

The tool may be a drilling bit to drill a hole through the component. The tool may comprise an EDM electrode to drill a hole through the component.

The tool may be a milling tool to mill a slot through the component. The tool may be a grinding tool to grind a slot through the component. The grinding tool may be a grinding wheel. The grinding tool may be a fir-tree shaped grinding tool.

The present disclosure also provides a method of machining a shape through a component comprising providing a tool at a first side of the component, positioning a light source in the path of the tool at the opposite side of the component, providing a camera at the first side of the component, the method comprising the steps of illuminating the second side of the component at least in the vicinity of the path of the tool, flowing a fluid over the surface of the light source to protect the light source, machining through the component from the first side of the component to the second side of the component to form the shape through the component, positioning the camera such that it has a line of sight view of the light source through the machined shape through the component, viewing the machined shape through the component using the illumination provided by the light source at the opposite side of the component, measuring parameters of the machined shape through the component using the view of the machine component provided by the camera, comparing the measured parameters of the machined shape through the component with required parameters for the machined shape through the component.

The light source may be a point light source or a diffuse light source.

The light source may be a light bulb, a light emitting diode (LED) or a fluorescent tube. The diffuse light source may be a panel comprising a plurality of LEDs or a diffusing reflector and a light source.

The method may comprise blowing the fluid over, e.g. across, the surface of the light source and/or sucking the fluid over, across, the surface of the light source. The method may comprise pumping the fluid over the surface of the light source and/or evacuating the fluid from the surface of the light source. If the fluid is a liquid the surface of the light surface may be arranged at an angle to the horizontal such that the fluid also flows across the surface of the light source under the action of gravity. The fluid source may comprise a pump to blow fluid, liquid or gas, and the fluid, liquid or gas, may be evacuated from the surface of the light source by a vacuum pump.

The method may comprise supplying the fluid from a supply nozzle.

The method may comprise positioning the supply nozzle at the opposite side of the component.

The method may comprise positioning the supply nozzle adjacent to the light source.

The supply nozzle may have an elongate outlet to provide a sheet of fluid over the light source.

The method may comprise supplying gas over the light source.

The method may comprise supplying high pressure gas over the light source.

The method may comprise supplying air, nitrogen or an inert gas over the light source.

The inert gas may be argon or neon.

The method may comprise drying and filtering the gas.

The method may comprise collecting the fluid using a collector nozzle.

The method may comprise positioning the collector nozzle at the opposite side of the component.

The method may comprise positioning the collector nozzle adjacent to the light source.

The collector nozzle may have an elongate inlet to collect a sheet of fluid after it has passed over the surface of the light source.

The collector nozzle and the supply nozzle may be positioned on opposite sides of the light source.

The component, the light source and the supply nozzle and/or the collector nozzle may remain in fixed positions relative to each other during the machining and viewing of the shape.

The method may comprise providing a transparent shield to further protect the light source.

The tool and camera may be positioned at a first side of the component and the light source is positioned at the opposite side of the component in use and the supply nozzle and/or the collection nozzle are positioned at the opposite side of the component.

The transparent shield may be sacrificial and/or abradable.

The transparent shield may be provided between the light source and the flow of gas or the flow of gas may be provided between the light source and the transparent shield. The transparent shield may be a sheet of glass or a sheet of polymeric material.

The method may comprise providing a laser source and laser machining a shape through the component. The method may comprise laser drilling a hole through the component.

The method may comprise providing the camera with a permanent line of sight view of the light source through the laser machined shape, providing an optical switch in the path of the laser beam, switching the optical switch between a first position for supplying the laser beam there-through to laser machine the shape through the component and a second position for allowing the camera to view the laser machined shape.

Alternatively the camera may be provided with a temporary line of sight view of the light source through the laser machined shape, moving the camera between a first position in which the camera is not in the optical path of the laser beam to allow the laser beam to laser machine the shape through the component and a second position in which the camera is in the optical path of the laser beam for allowing the camera to view the laser machined shape.

The method may comprise mounting the camera on a robotic arm.

The method may comprise mounting the camera on the laser source but offset from optical axis of the laser beam, moving the laser source and the camera together so that the camera is in the optical path used by the laser beam to machine the shape for allowing the camera to view the laser machined shape.

The method may comprise re-drilling a laser drilled hole in the component if the measured parameters do not satisfy at least one of the required parameters for the laser drilled hole or terminating the laser drilling of the hole if the measured parameters of the laser drilled hole satisfy the required parameters.

The method may comprise providing a drilling bit and drilling a hole through the component. The method may comprise providing an EDM electrode and drilling a hole through the component. The drilling bit, EDM electrode or laser beam may drill a hole through a combustion chamber wall, a combustion chamber tile, a combustion chamber segment, a combustion chamber heat shield, a turbine blade, a turbine vane or other gas turbine engine component.

The method may comprise providing a milling tool and milling a slot through the component. The method may comprise providing a grinding tool and grinding a slot through the component. The grinding tool may be a grinding wheel. The grinding tool may be a fir-tree shaped grinding tool.

The fir-tree shaped grinding tool may machine a slot through a turbine disc or a compressor disc.

The present invention also provides an apparatus for laser drilling a hole comprises a laser source, a light source, a camera, a processor, the light source is positioned in the path of the laser beam, the camera is positioned or positionable such that it has a line of sight view of the light source through the laser drilled hole, the processor is arranged to measure the parameters of the laser drilled hole using the view of the laser drilled hole provided by the camera, the processor is arranged to compare the measured parameters of the laser drilled hole with required parameters for the laser drilled hole and a device is arranged to provide a flow gas over the surface of the light source.

The camera may be positioned such that it has a permanent line of sight view of the light source through the laser drilled hole, an optical switch is provided in the path of the laser beam, the optical switch is switchable between a first position for supplying the laser beam there-through to laser drill the hole through the component and a second position for allowing the camera to view the laser drilled hole.

The camera may be positioned such that it has a temporarily line of sight view of the light source through the laser drilled hole, the camera is movable between a first position in which the camera is not in the optical path of the laser beam to allow the laser beam to laser drill the hole through the component and a second position in which the camera is in the optical path of the laser beam for allowing the camera to view the laser drilled hole.

The camera may be mounted on a robotic arm.

The camera may be mounted on the laser source but offset from optical axis of the laser beam, the laser source and the camera are movable together so that the camera is in the optical path used by the laser beam to drill the hole for allowing the camera to view the laser drilled hole.

If the processor determines that the measured parameters of the laser drilled hole do not satisfy at least one of the required parameters for the laser drilled hole the laser source may be arranged to re-drill the laser drilled hole in the component or if the processor determines that the measured parameters of the laser drilled hole satisfy the required parameters of the laser drilled hole the processor is arranged to terminate the laser drilling.

The present invention also provides a method of laser drilling a hole comprising providing a laser source at a first side of a component, positioning a light source in the path of the laser beam at the opposite side of the component, providing a camera at the first side of the component, the method comprising the steps of illuminating the second side of the component at least in the vicinity of the path of the laser beam, flowing a gas over the surface of the light source to protect the light source, laser drilling a hole through the component from the first side of the component, positioning the camera such that it has a line of sight view of the light source through the laser drilled hole, viewing the laser drilled hole in the component using the illumination provided by the light source at the opposite side of the component, measuring parameters of the laser drilled hole using the view of the laser drilled hole provided by the camera, comparing the measured parameters of the laser drilled hole with required parameters for the laser drilled hole.

The method may comprise providing the camera with a permanent line of sight view of the light source through the laser drilled hole, providing an optical switch in the path of the laser beam, switching the optical switch between a first position for supplying the laser beam there-through to laser drill the hole through the component and a second position for allowing the camera to view the laser drilled hole.

The method may comprise providing the camera with a temporary line of sight view of the light source through the laser drilled hole, moving the camera between a first position in which the camera is not in the optical path of the laser beam to allow the laser beam to laser drill the hole through the component and a second position in which the camera is in the optical path of the laser beam for allowing the camera to view the laser drilled hole.

The method may comprise mounting the camera on a robotic arm.

The method may comprise mounting the camera on the laser source but offset from optical axis of the laser beam, moving the laser source and the camera together so that the camera is in the optical path used by the laser beam to machine the shape for allowing the camera to view the laser machined shape.

If the measured parameters of the laser drilled hole do not satisfy at least one of the required parameters for the laser drilled hole the method may comprise re-drilling the laser drilled hole in the component or if the measured parameters of the laser drilled hole satisfy the required parameters of the laser drilled hole the method may comprise terminating the laser drilling.

BRIEF DESCRIPTION OF THE DRAWINGS

The present disclosure will be more fully described by way of example with reference to the accompanying drawings, in which:—

FIG. 3 is a further enlarged perspective view of a portion of an outer annular wall of a combustion chamber, shown in FIG. 2, having a laser drilled hole inspected according to the present disclosure.

FIG. 8 is an enlarged schematic view of an alternative arrangement of transparent shield and gas supply nozzles of an apparatus for inspecting a laser drilled hole shown in FIG. 6.

FIG. 9 is a perspective view of an alternative light source and a gas supply nozzle of the apparatus for inspecting a laser drilled hole shown in FIG. 4.

DETAILED DESCRIPTION

Figure 1:
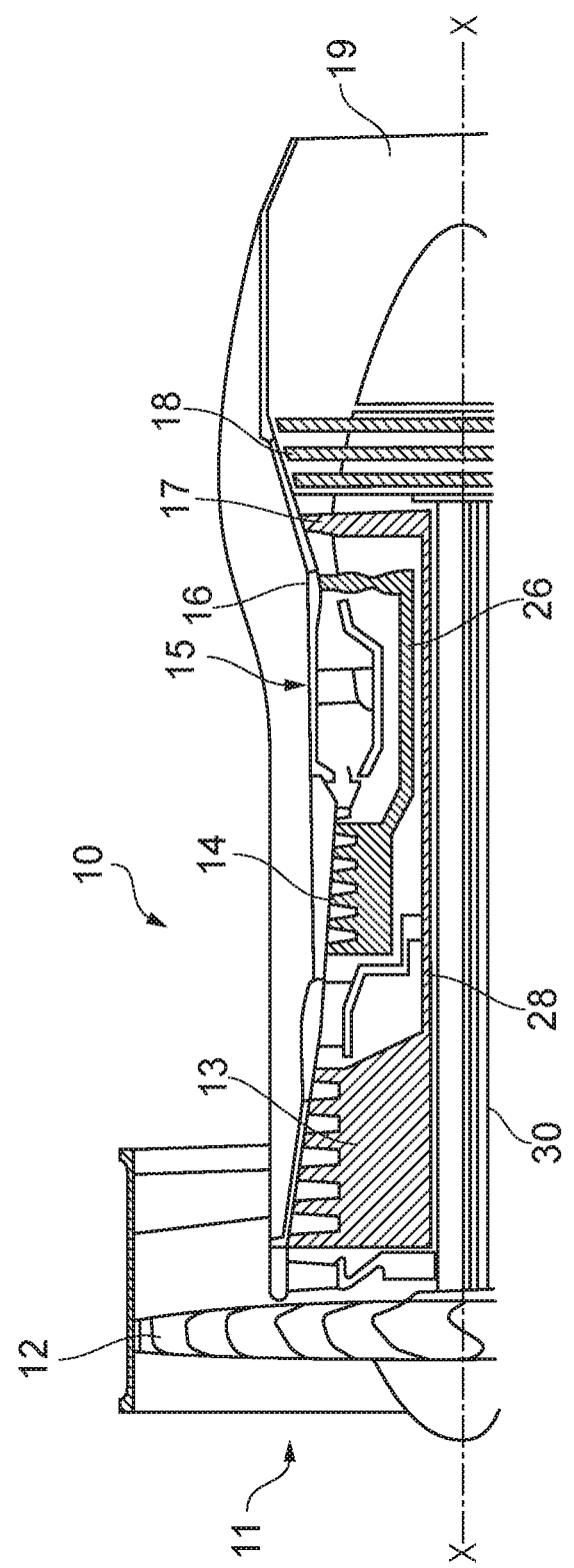
FIG. 1 is partially cut away view of a turbofan gas turbine engine having a component inspected according to the present disclosure.

A turbofan gas turbine engine 10, as shown in FIG. 1, comprises in flow series an intake 11, a fan 12, an intermediate pressure compressor 13, a high pressure compressor 14, a combustion chamber 15, a high pressure turbine 16, an intermediate pressure turbine 17, a low pressure turbine 18 and an exhaust 19. The high pressure turbine 16 is arranged to drive the high pressure compressor 14 via a first shaft 26. The intermediate pressure turbine 17 is arranged to drive the intermediate pressure compressor 13 via a second shaft 28 and the low pressure turbine 18 is arranged to drive the fan 12 via a third shaft 30. In operation air flows into the intake 11 and is compressed by the fan 12. A first portion of the air flows through, and is compressed by, the intermediate pressure compressor 13 and the high pressure compressor 14 and is supplied to the combustion chamber 15. Fuel is injected into the combustion chamber 15 and is burnt in the air to produce hot exhaust gases which flow through, and drive, the high pressure turbine 16, the intermediate pressure turbine 17 and the low pressure turbine 18. The hot exhaust gases leaving the low pressure turbine 18 flow through the exhaust 19 to provide propulsive thrust. A second portion of the air bypasses the main engine to provide propulsive thrust.

Figure 2:
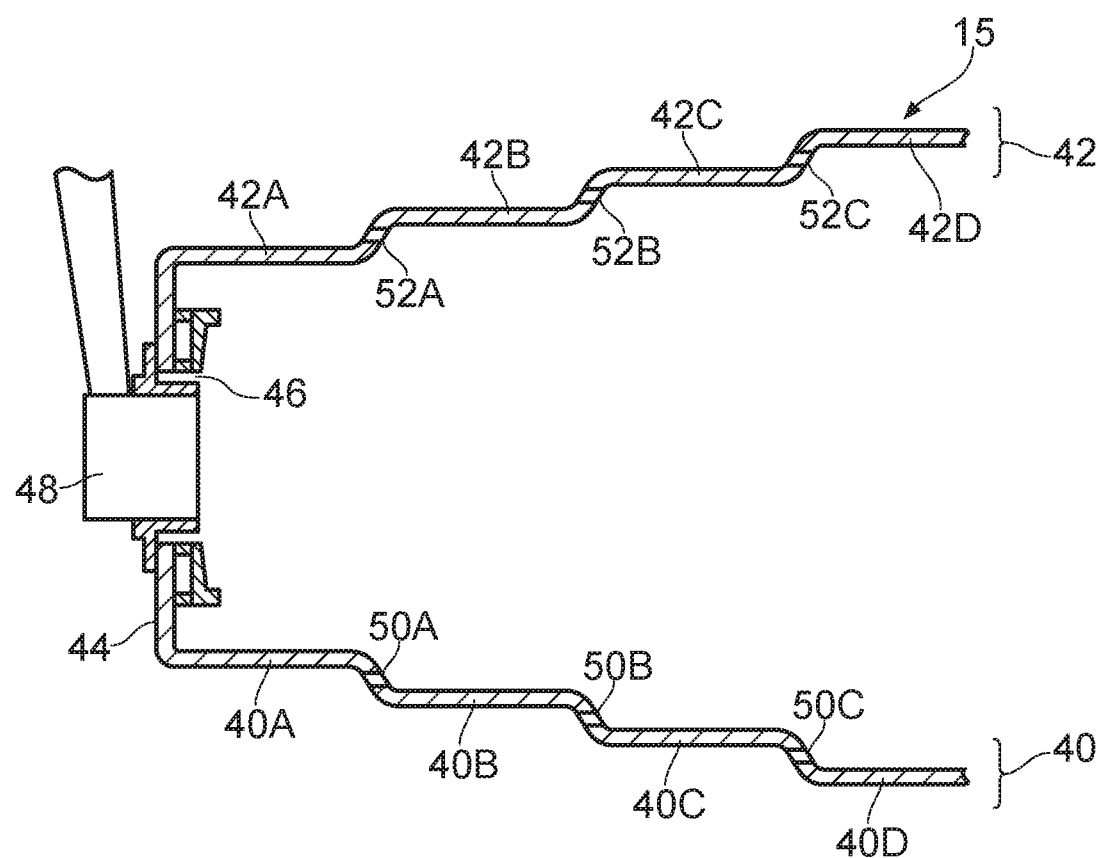
FIG. 2 is an enlarged cross-sectional view of a combustion chamber, shown in FIG. 1, having a laser drilled hole inspected according to the present disclosure.

The combustion chamber 15, as shown more clearly in FIG. 2, is an annular combustion chamber and comprises a radially inner annular wall structure 40, a radially outer annular wall structure 42 and an upstream end wall structure 44. The upstream end of the first annular wall 46 is secured to the upstream end wall structure 44 and the upstream end of the third annular wall 50 is secured to the upstream end wall structure 44. The upstream end wall structure 44 has a plurality of circumferentially spaced apertures 46 and each aperture 46 has a respective one of a plurality of fuel injectors 48 located therein. The fuel injectors 48 are arranged to supply fuel into the annular combustion chamber 15 during operation of the gas turbine engine 10. The radially inner annular wall structure 40 has a radially stepped structure and the radially outer annular wall structure 42 has a radially stepped structure.

The radially inner annular wall structure 40 comprises a plurality of portions 40A, 40B, 40C and 40D arranged at different radii separated by Z-rings 50A, 50B and 50C. The radially outer annular wall structure 42 comprises a plurality of portions 42A, 42B, 42C and 42D arranged at different radii separated by Z-rings 52A, 52B and 52C. The Z-rings 50A, 50B and 50C have a plurality of cooling holes extending there-through to supply coolant from the outer surface of the first annular wall structure 40 onto the inner surface of the first annular wall structure 40 and the Z-rings 52A, 52B and 52C have a plurality of cooling holes extending there-through to supply coolant from the outer surface of the second annular wall structure 42 onto the inner surface of the second annular wall structure 42. Each of the Z-ring 50A, 50B, 50C, 52A, 52B and 52C has a plurality of radially spaced rows of cooling holes and the cooling holes in each row of cooling holes are circumferentially spaced apart throughout the full circumference of the respective Z-ring. The cooling holes in adjacent rows are generally arranged such that they are staggered circumferentially.

A portion of the radially outer annular wall structure 42 is shown more clearly in FIG. 3, and the portions 42A, 42B, 42C and 42D separated by the Z-rings 52A, 52B and 52C are clearly seen. The Z-rings 52A, 52B and 52C have portions extending generally radially and in this example each of the Z-rings 52A, 52B and 52C has three rows of cooling holes 54A, 54B and 54C extending generally axially through the radially extending portion of the respective Z-ring 52A, 52B and 52C. The cooling holes 54A, 54B and 54C are produced in the Z-rings 52A, 52B and 52C by laser drilling.

As mentioned previously it is necessary to inspect the laser drilled cooling holes 54A, 54B, 54C to ensure that they are in the required position, have the required dimensions, the required shape and the required angle of orientation etc.

Figure 4:
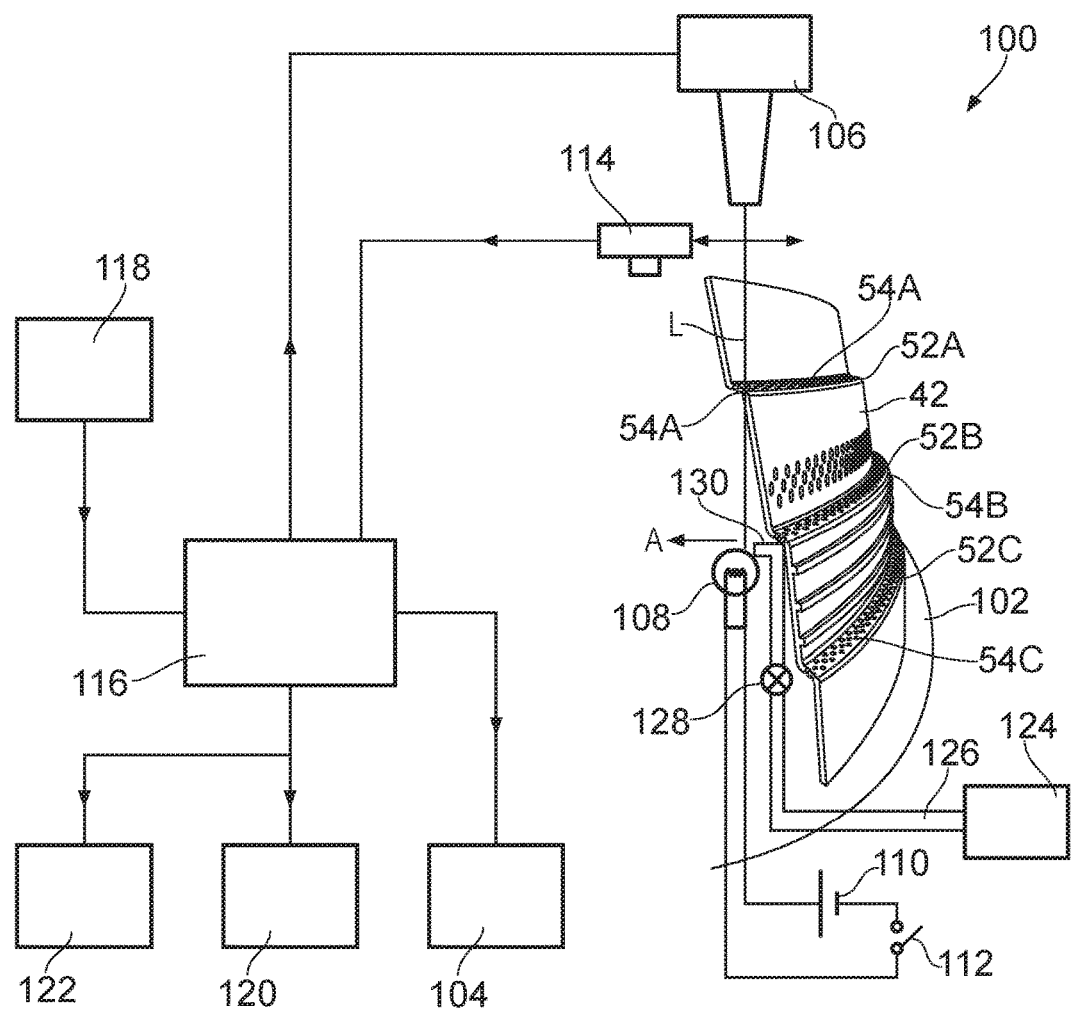
FIG. 4 is a schematic of an apparatus for inspecting a laser drilled hole according to the present disclosure.

An apparatus 100 for inspecting a laser drilled cooling hole according to the present disclosure is shown in FIG. 4. The apparatus 100 comprises a support 102 for the component to be laser drilled. In this example the component is the radially outer annular wall structure 42 and the support 102 is a turntable and the radially outer annular wall structure 42 is mounted coaxially on the turntable 102. The turntable 102 is driven by a motor 104 so that the turntable 102 rotates incrementally so that the cooling holes in each of the rows of cooling holes 54A, 54B and 54C may be laser drilled sequentially one by one. A laser source, a laser gun, 106 is provided to drill through the component 42 to produce the cooling holes using a laser beam L. The laser source 106 is mounted such that it is movable radially with respect to the axis of the turntable 102 so that the different rows of cooling holes 54A, 54B and 54C at different radii may be drilled through the Z-rings 52A, 52B and 52C. A light source 108 is provided to illuminate the laser drilled cooling holes so that they may be inspected and the light source 108 is electrically connected to an electrical power supply 110 via an electrical switch 112. A camera 114 is provided to view the laser drilled cooling holes illuminated by the light source 108. The camera 114 is positioned, or positionable, such that it has a line of sight view of the light source 108 through the laser drilled hole. This may involve positioning the camera 114 in the path of the laser beam L when the laser source 106 is not operating. The apparatus 100 also comprises a processor 116, a database 118 of acceptable parameters for a laser drilled cooling hole, a monitor 120 and a store 122 for recording the parameters of the laser drilled cooling holes. The processor 116 is arranged to receive one or more images of a laser drilled cooling hole, the processor 116 is arranged to measure the parameters of the laser drilled cooling hole using the view of the laser drilled hole provided by the camera 114 and the processor 116 is arranged to compare the measured parameters of the laser drilled cooling hole with the required parameters for a laser drilled cooling hole. The processor 116 is also arranged to control the laser source 106 and the motor 104 for the turntable 102. The processor 116 may be a computer or personal computer. The apparatus 100 also comprises a source of gas 124 and the gas source 124 is arranged to supply gas at a suitable pressure and flow rate through a pipe 126 and valve 128 to a supply nozzle 130. The supply nozzle 130 is positioned in proximity to the light source 108 and is arranged to provide a flow of gas A over the surface of the light source 108. The pipe 126 may also have a drier and a filter such that the gas is dried and filtered before it is supplied to the supply nozzle 130.

Using the light source 108 to "backlight" the laser drilled effusion cooling hole provides good contrast between the laser drilled cooling hole and the component 42 and enables the use of edge detection software to determine the edge of the laser drilled cooling hole in the component 42. The camera 114 is arranged to view the laser drilled cooling hole and the associated processor 116 with edge detection software determines if the laser drilled cooling hole conforms to the required position, dimensions and shape etc.

The camera 114 may be provided permanently in the path of the laser beam L, an optical switch is provided in the path of the laser beam L and the optical switch is switchable between a first position for supplying the laser beam L there-through to laser drill the cooling hole through the component 42 and a second position for allowing the camera 114 to view the laser drilled hole using the same optical path as the laser beam L, e.g. the laser beam L and the camera 114 sequentially use the same optical path. The optical switch may be a mirror. In this arrangement the component 42, the light source 108 and the supply nozzle 130 remain in fixed positions relative to each other during the drilling and viewing of each effusion cooling hole. The laser source 106 and the camera 114 also remain in substantially fixed positions relative to the component 42, the light source 108 and the supply nozzle 130 except for any relative movements of the laser source 106, and hence the camera 114, required to drill each effusion cooling hole.

The camera 114 may be temporarily in the path of the laser beam L, the camera 114 is movable between a first position in which the camera 114 is not in the optical path of the laser beam L to allow the laser beam L to laser drill the cooling hole through the component 42 and a second position in which the camera 114 is in the optical path of the laser beam L for allowing the camera 114 to view the laser drilled hole. The camera 114 may be mounted on a robotic arm. In this arrangement the component 42, the light source 108 and the supply nozzle 130 also remain in fixed positions relative to each other during the drilling and viewing of each effusion cooling hole. The laser source 106 also remains in a substantially fixed position relative to the component 42, the light source 108 and the supply nozzle 130 except for any relative movements of the laser source 106 required to drill each effusion cooling hole. The camera 114 is moved between the first and second positions to enable the laser source 106 to drill the effusion cooling hole and to enable the camera 114 to view the drilled effusion cooling hole respectively.

Alternatively the camera 114 may be mounted on the laser source 106, but offset from optical axis of the laser beam L. The laser source 106 and the camera 114 are movable together so that the camera 114 is in the optical path used by the laser beam L to drill the hole for allowing the camera 114 to view the laser drilled hole. In this arrangement the component 42, the light source 108 and the supply nozzle 130 also remain in fixed positions relative to each other during the drilling and viewing of each effusion cooling hole. The laser source 106 and the camera 114 are moved together between the two positions.

The light source 108 may be a point light source or a diffuse light source. The light source may be a light bulb, a light emitting diode (LED) or a fluorescent tube. The light bulb may be a tungsten filament bulb, a halogen bulb or an energy saving bulb. The diffuse light source may be a panel comprising a plurality of LEDs or a diffusing reflector and a light source.

It is to be noted that the apparatus is arranged such that the laser source 106 is provided at a first side of a component 42, the light source 108 is positioned in the path of the laser beam L at the opposite side of the component 42 and the camera 114 is provided at the first side of the component 42. In addition it is also to be noted that the supply nozzle 130 is positioned at the opposite side of the component 42.

The source of gas 124 may be a source of high pressure gas, e.g. compressed air, high pressure nitrogen from a gas bottle, high pressure argon from a gas bottle or other suitable inert gas, e.g. neon, from a gas bottle. The source of gas 124 may comprise a pump to blow the gas at high pressure, e.g. compressed air, over the surface of the light source 108.

Figure 5:
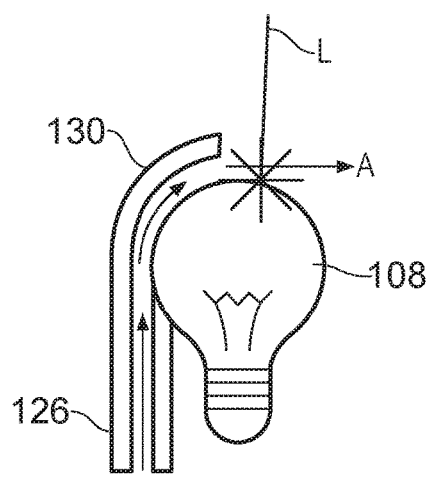
FIG. 5 is an enlarged schematic view of a gas supply nozzle of the apparatus for inspecting a laser drilled hole shown in FIG. 4.

FIG. 5 shows an arrangement in which the supply nozzle 130 is positioned immediately adjacent to the light source 108 so that the gas flow A is immediately over the surface of a light bulb 108.

In operation the second side of the component 42 is illuminated at least in the vicinity of the path of the laser beam L, a gas A is flowed over the surface of the light source 108 to protect the light source 108, a cooling hole is laser drilled through the component 42 using the laser beam L form the laser source 106, the camera 114 is positioned such that it has a line of sight view of the light source 108 through the laser drilled hole. As mentioned previously this may involve positioning the camera 114 temporarily in the path of the laser beam L when the laser source 106 is not operating. The laser drilled cooling hole in the component 42 is viewed using the illumination provided by the light source 108 at the opposite side of the component 42. The parameters of the laser drilled cooling hole are measured by the processor 116 using the view of the laser drilled cooling hole provided by the camera 114. The measured parameters of the laser drilled cooling hole are compared with required parameters for the laser cooling drilled hole supplied by the database 118 in the processor 116. If the processor 116 determines that the measured parameters of the laser drilled cooling hole do not satisfy at least one of the required parameters for the laser drilled cooling hole the processor 116 re-drills the laser drilled cooling hole in the component 42. Alternatively, if the processor 116 determines that the measured parameters of the laser drilled cooling hole do not satisfy at least one of the required parameters for the laser drilled cooling hole the processor 116 leaves that cooling hole as a non-conforming cooling hole and laser drills the next cooling hole in the component 42 such that it corrects, or compensates, for the non-conforming cooling hole or calculates an appropriate offset for the next cooling hole in the component 42 so that it conforms to the required parameters for the laser drilled hole. A single non-conforming cooling hole in a large array of cooling holes will have a minimal effect on the cooling performance of the component.

If the processor 116 determines that the measured parameters of the laser drilled cooling hole satisfy the required parameters for the laser drilled cooling hole the laser drilling of that cooling hole is terminated and the processor 116 instructs the motor 104 to rotate the turntable 102 by one increment to laser drill the next cooling hole in the component 42 and the processor 116 may instruct the laser source 106 to move radially outwardly, or radially inwardly, to laser drill cooling holes in another row of cooling apertures.

The advantage of the present disclosure is that it enables in process inspection of laser drilling machines or laser drilling process using back lighting. The present disclosure allows the light source to remain static in the path of the laser beam and avoids the need for complex mechanisms to move the light source into and out of the path of the laser beam. The present disclosure ensures that the lighting, lumen, level remains substantially constant and enables comparative measurements to be made. The present disclosure reduces, or prevents, the dross, dust, spatter, e.g. the molten material droplets and/or molten material droplets which have cooled and solidified, produced by the laser beam drilling through the component collecting, e.g. depositing or settling, on the light source and hence prevents, or reduces, the light output from the light source reducing and thus makes the comparative measurements easier. The present disclosure also reduces the surface temperature of the light source caused by the incident laser beam striking the light source once it has drilled through the component and thereby reduces degradation of the light source and improves the working life of the light source. An additional advantage is that it has been found that the flow of gas also reduces, or prevents, dross, dust, or spatter, e.g. the molten material droplets and/or molten material droplets which have cooled and solidified, produced by the laser beam drilling through the component collecting, e.g. depositing or settling, on the surface of the component and/or reduces, or prevents, dross, dust, or spatter produced by the laser beam drilling through the component collecting, e.g. depositing or settling, in one or more previously drilled holes.

Figure 6:
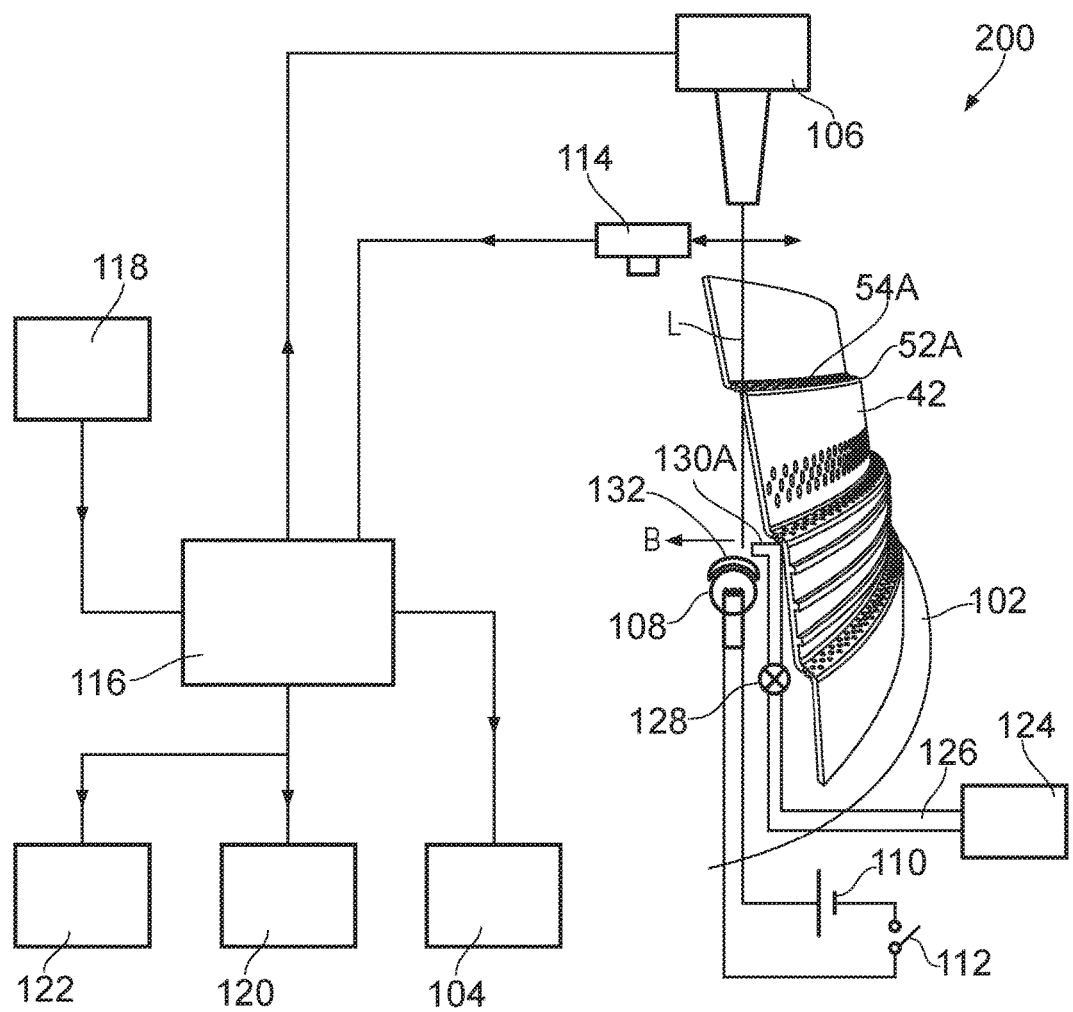
FIG. 6 is a schematic of an alternative apparatus for inspecting a laser drilled hole according to the present disclosure.
Figure 7:
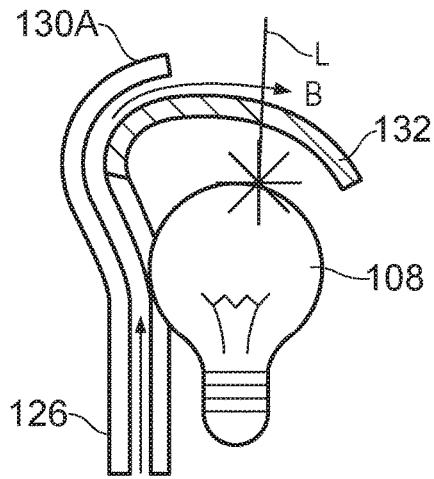
FIG. 7 is an enlarged schematic view of a transparent shield and a gas supply nozzle of the apparatus for inspecting a laser drilled hole shown in FIG. 6.

A further apparatus 200 for inspecting a laser drilled cooling hole according to the present disclosure is shown in FIGS. 6 and 7. The apparatus 200 is substantially the same as the apparatus 100 shown in FIG. 4 and like parts are denoted by like numerals. The apparatus 200 differs in that it also comprises a transparent shield 132 to further protect the light source 108. The transparent shield 132 is provided between the light source 108 and the flow of gas B from the supply nozzle 130A. However, the flow of gas from the nozzle may be provided between the light source and the transparent shield. The transparent shield 132 may be a sheet of glass or a sheet of polymeric material, e.g. transparent polytetrafluoroethylene (PTFE). The transparent shield may be sacrificial and/or abradable. Again it is to be noted that the supply nozzle 130A is positioned at the opposite side of the component 42.

The use of the transparent shield provides additional reduction of the surface temperature of the light source, reduction of degradation of the light source and improves working life of the light source. The use of the transparent shield also prevents the dross, dust, spatter produced by the laser beam drilling through the component collecting on the light source and hence prevents, or reduces, the light output from the light source reducing and thus makes the comparative measurements easier. The flow of gas over the surface of the transparent shield reduces, or prevents, the dross, dust, spatter produced by the laser beam drilling through the component collecting on the transparent shield and hence prevents, or reduces, the light output from the light source reducing and thus makes the comparative measurements easier.

In FIG. 8 two nozzles 130C and 130D are arranged to provide two flows of gas, one flow of gas C across and over the transparent shield 132A and one flow of gas D between the light source 108 and the transparent shield 132A.

In FIG. 9 the light source 108A is a diffuse light source comprising a light emitting panel comprising a plurality of LEDs. Alternatively, the diffuse light source 108A may comprise a reflective panel which comprises a diffused reflector and a separate light source arranged to direct light onto the diffused reflector. The light source 108A has a planar surface and an elongate supply nozzle 130E provides a flow of gas E across and over the planar surface of the light source 108A. The flow of gas E is in the form of a sheet of gas which flows across the whole of the surface of the light source 108A. The elongate supply nozzle 130E has an elongate outlet slot 134E through which the gas E flows and the elongate outlet slot 134E is arranged parallel to the surface of the planar surface of the light source 108A. Alternatively, the elongate supply nozzle 130E may be used with a fluorescent tube so that the elongate outlet slot 134E is arranged parallel to the axis of the fluorescent tube. The elongate outlet slot 134E extends linearly in this example.

Figure 10:
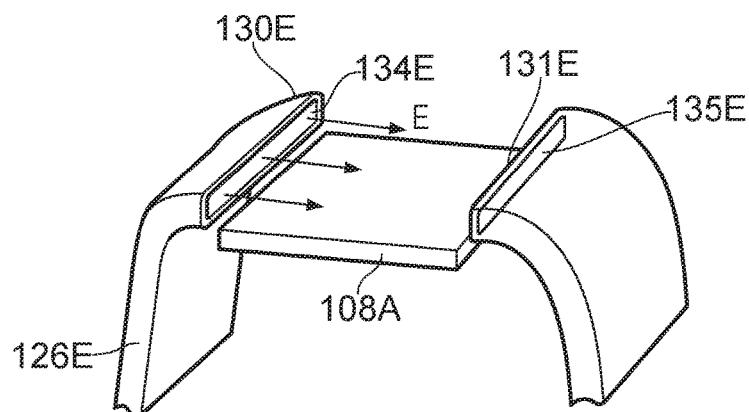
FIG. 10 is a perspective view of an alternative light source, a gas supply nozzle and a gas collection nozzle of the apparatus for inspecting a laser drilled hole shown in FIG. 4.

In FIG. 10 the light source 108A is a diffuse light source comprising a light emitting panel comprising a plurality of LEDs. Alternatively, the diffuse light source 108A may comprise a reflective panel which comprises a diffused reflector and a separate light source arranged to direct light onto the diffused reflector. The light source 108A has a planar surface and an elongate supply nozzle 130E provides a flow of gas E across and over the planar surface of the light source 108A. The flow of gas E is in the form of a sheet of gas which flows across the whole of the surface of the light source 108A. The elongate supply nozzle 130E has an elongate outlet slot 134E through which the gas E flows and the elongate outlet slot 134E is arranged parallel to the surface of the planar surface of the light source 108A.

Alternatively, the elongate supply nozzle 130E may be used with a fluorescent tube so that the elongate outlet slot 134E is arranged parallel to the axis of the fluorescent tube. The elongate outlet slot 134E extends linearly in this example. In addition a further elongate collection nozzle 131E is arranged to collect the flow of gas E which has passed across the planar surface of the light source 108A. The elongate nozzle 131E also has an elongate inlet slot 135E through which the gas E flows and the elongate inlet slot 135E is arranged parallel to the surface of the planar surface of the light source 108A. The elongate nozzle 131E is connected to a pump, e.g. a vacuum pump, such that the elongate nozzle 131E sucks the fluid over, across, the surface of the light source 108A. The elongate inlet slot 135E extends linearly in this example.

In other arrangements the elongate outlet slot and/or the elongate inlet slot may be arcuate for example with a curved light source, e.g. a light bulb.

It is to be noted that the laser drilled cooling holes have a diameter typically in the range of 0.4 mm to 0.8 mm, but smaller or larger diameter holes may be drilled.

The nozzle, in any of the embodiments relating to laser drilling, may be shaped such that a portion of the gas flow is directed towards the surface of the component to reduce, or prevent, dross, dust, or spatter from the laser drilling through the component collecting, e.g. depositing or settling, on the surface of the component and/or reduce, or prevent, dross, dust, or spatter from the laser drilling through the component collecting, e.g. depositing or settling, in a previously drilled hole through the component. Alternatively, the nozzle, in any of the embodiments relating to laser drilling, may be shaped such that a portion of the gas flow is directed towards the surface of the component to remove dross, dust, or spatter from the laser drilling through the component which has collected, e.g. deposited or settled, on the surface of the component and/or to remove dross, dust, or spatter from the laser drilling through the component which has collected, e.g. deposited or settled, in a previously drilled hole through the component.

Figure 11:
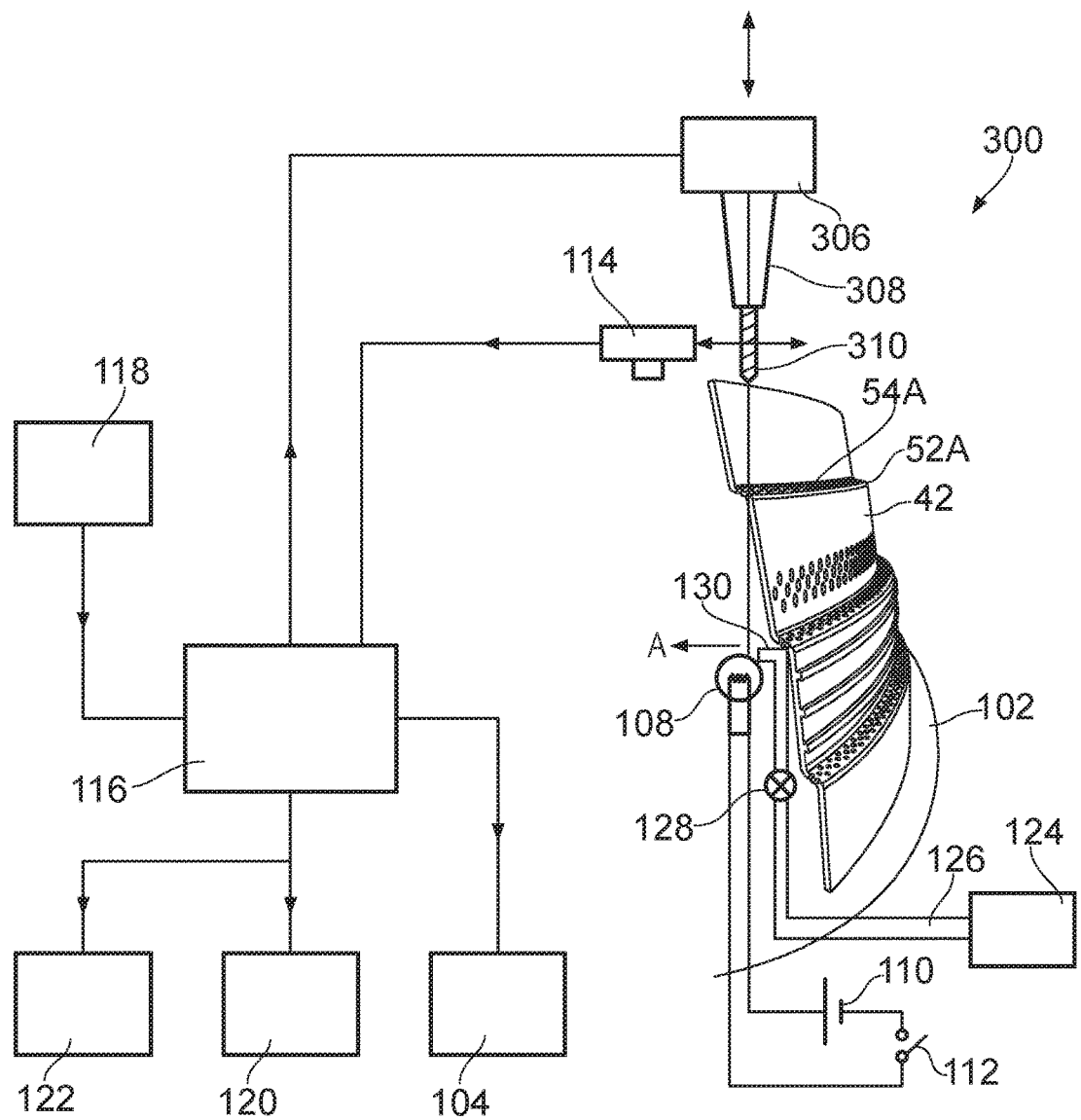
FIG. 11 is a schematic of an apparatus for inspecting a machine drilled hole according to the present disclosure.

A further apparatus 300 for inspecting a machine drilled cooling hole according to the present disclosure is shown in FIG. 11. The apparatus 300 is substantially the same as the apparatus 100 shown in FIG. 4 and like parts are denoted by like numerals. The apparatus 300 differs in that it comprises a drilling machine 306 including a chuck 308 and a drilling tool, e.g. a drill bit, 310 instead of a laser source. The drill bit 310 is rotated about its axis and moved axially with respect to the drill bit 310 towards the radially outer annular wall structure 42 to drill a cooling hole through the radially outer annular wall structure 42. In addition it is to be noted that the supply nozzle 130 is positioned at the opposite side of the radially outer annular wall structure 42. A transparent shield may be provided between the light source 108 and the flow of gas B from the supply nozzle 130A, in a similar manner to that shown in FIGS. 6 and 7. The transparent shield may be a sheet of glass or a sheet of polymeric material, e.g. transparent polytetrafluoroethylene (PTFE). The transparent shield may be sacrificial and/or abradable. In this arrangement the component 42, the light source 108 and the supply nozzle 130 also remain in fixed positions relative to each other during the drilling and viewing of each effusion cooling hole. The drill bit 310 also remains in a substantially fixed position relative to the component 42, the light source 108 and the supply nozzle 130 except for any relative axial movements of the drill bit 310 required to drill each effusion cooling hole. The camera 114 is moved relatively to the component 42, the light source 108 and the supply nozzle 130 between the first and second positions to enable the drill bit 310 to drill the effusion cooling hole and to enable the camera 114 to view the drilled effusion cooling hole respectively.

The advantage of this embodiment of the present disclosure is that it enables in process inspection of drilling machines or machine drilling process using back lighting. The present disclosure allows the light source to remain static in the path of the drill bit and avoids the need for complex mechanisms to move the light source into and out of the path of the drill bit. The present disclosure ensures that the lighting, lumen, level remains substantially constant and enables comparative measurements to be made. The present disclosure reduces, or prevents, the material particles, dust, machining swarf produced by the drill bit drilling through the component collecting, e.g. depositing or settling, on the light source and hence prevents, or reduces, the light output from the light source reducing and thus makes the comparative measurements easier.

Although the present disclosure has referred to laser drilling and mechanically drilling cooling holes in a Z-ring of a combustion chamber wall it is equally applicable to laser drilling, mechanically drilling or electro-discharge machining, impingement cooling holes in a combustion chamber wall or a combustion chamber segment, and it is also applicable to laser drilling, mechanically drilling or electro-discharge machining effusion cooling holes in a combustion chamber tile, a combustion chamber segment, a combustion chamber heat shield, a turbine blade or a turbine vane or other gas turbine engine component.

Although the present disclosure has been described with reference to cooling holes it is equally applicable to holes in other component and/or holes for other purposes. The holes may be circular, elliptical, race-track shape or any other suitable shape in cross-section. The holes may be arranged perpendicularly to the side/surface of the component or may be arranged at an angle to the side/surface of the component. The present disclosure is equally applicable to laser percussion drilling and to laser trepanning drilling of holes though a component.

Although the present disclosure has been described with reference to laser drilling holes it is equally applicable to laser cutting a shape, or shapes, through a component, e.g. laser cutting a slot.

Figure 12:
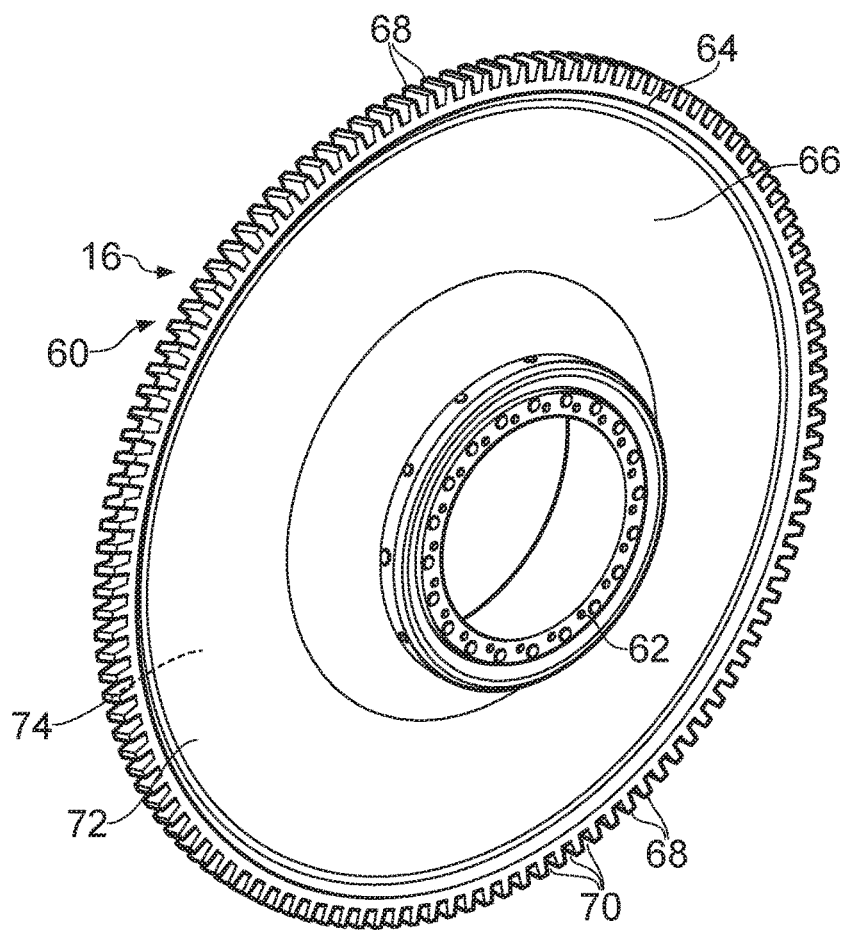
FIG. 12 is an enlarged perspective view of a turbine disc, shown in FIG. 1, having a machined slot inspected according to the present disclosure.
Figure 13:
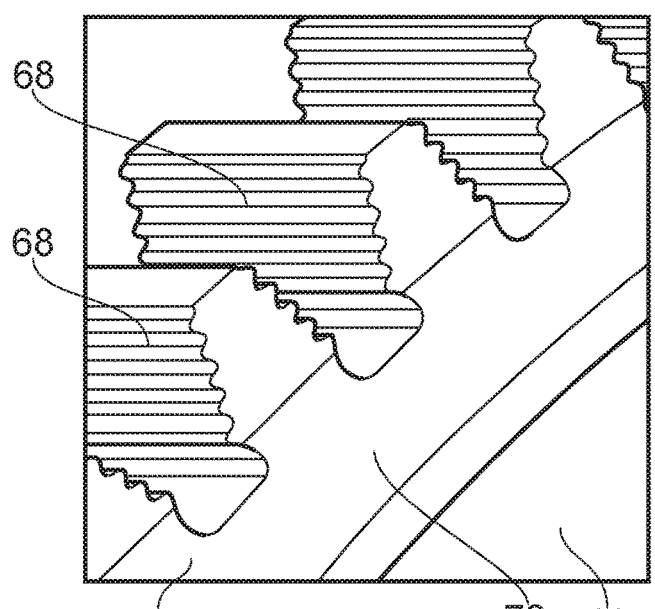
FIG. 13 is a further enlarged perspective view of a portion of the rim of the turbine disc shown in FIG. 12 showing machined slots.

The high-pressure turbine 16, as shown in FIGS. 11 and 12, comprises a turbine disc 60. The turbine disc 60 includes a hub 62 and a rim 64 connected by a diaphragm 66. The rim 64 of the turbine disc 60 has a plurality of circumferentially spaced fir-tree shaped slots 70 which produce a plurality of circumferentially spaced fir-tree shaped projections 68. Each fir-tree shaped slot 70 is arranged to receive a fir-tree shaped root of a turbine blade (not shown). The fir-tree shaped slots 70 extend axially through the rim 66 of the turbine disc 60 from an axially upstream face 72 to an axially downstream face 74 of the turbine disc 60. The upstream end of each fir-tree shaped slot 70 is circumferentially displaced from the associated downstream end of the fir-tree shaped slot 70.

Figure 14:
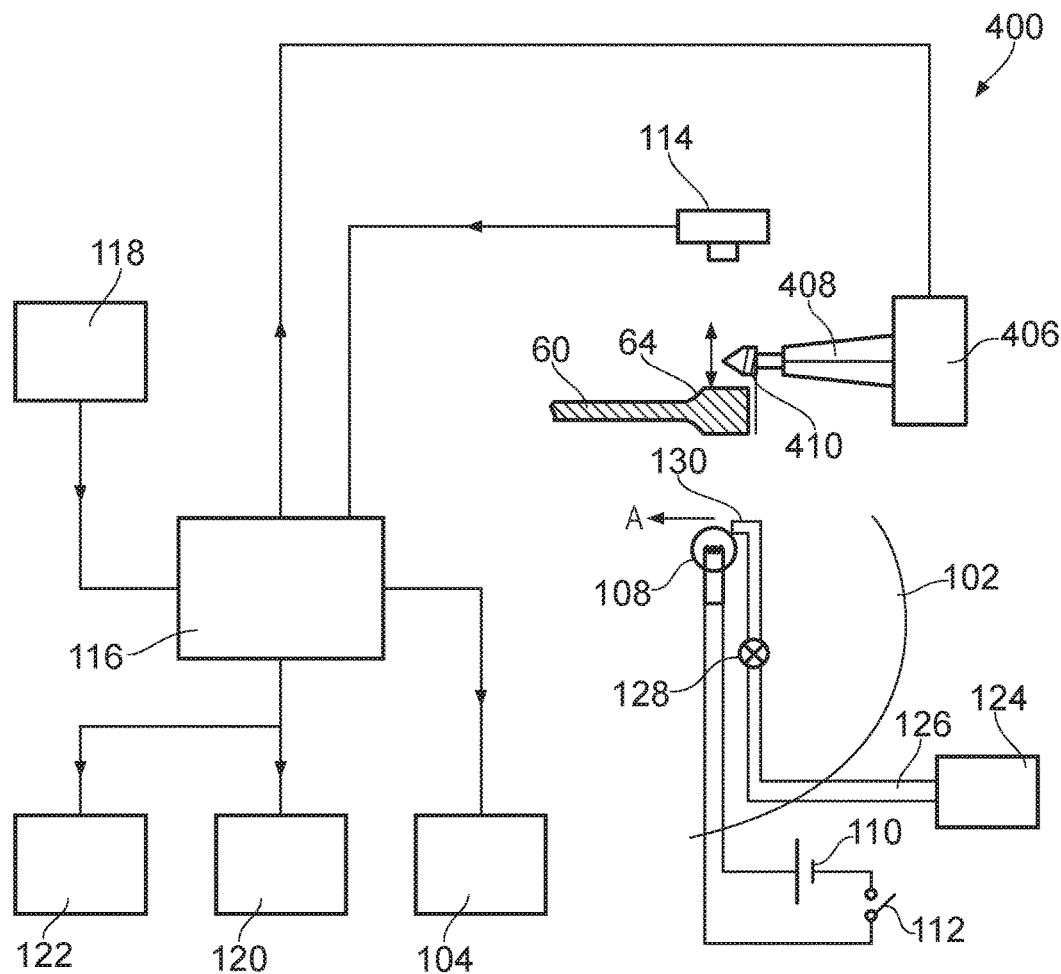
FIG. 14 is a schematic of an apparatus for inspecting a machined slot according to the present disclosure.

A further apparatus 400 for inspecting a machined fir-tree shaped slot according to the present disclosure is shown in FIG. 14. The apparatus 400 is substantially the same as the apparatus 300 shown in FIG. 11 and like parts are denoted by like numerals. The apparatus 400 differs in that it comprises a machine 406 including a chuck 408 and a tool, a milling cutter or grinding tool, 410. The machine 406 may be a multi-axis machine, e.g. a computer numerically controlled (CNC) 5 axis machine. The milling tool or grinding tool 410 is rotated about its axis and the milling tool or grinding tool 410 and turbine disc 60 are moved relative to each other such that the milling tool or grinding tool 410 moves towards the rim 64 of the turbine disc 60 and axially across, the rim 64 of the turbine disc 60 to mill or grind a fir-tree shaped slot 70 through the rim 64 of the turbine disc 60. The fir-tree shaped slot 70 may be formed by initially forming, machining, a straight sided rough slot and then forming, machining, a finished fir-tree shaped slot 70. The rough slot may also be formed by milling or grinding. The finished fir-tree shaped slot 70 may be formed using a fir-tree shaped milling tool or grinding tool, as shown in FIG. 14. Alternatively, the fir-tree shaped slot 70 may be formed by initially forming, machining, a fir-tree shaped rough slot and then forming, machining, a finished fir-tree shaped slot 70. The rough slot and the finished slot may be formed by milling or the rough slot and the finished slot may be formed by grinding. The rough fir-tree shaped slot and the finished fir-tree shaped slot 70 may be formed using respective roughing and finishing fir-tree shaped milling, or grinding, tools, as shown in FIG. 14. It is also to be noted that the supply nozzle 130 is positioned at the opposite side of the turbine disc 60. A transparent shield may be provided between the light source 108 and the flow of gas B from the supply nozzle 130A, in a similar manner to that shown in FIGS. 6 and 7. The transparent shield may be a sheet of glass or a sheet of polymeric material, e.g. transparent polytetrafluoroethylene (PTFE). The transparent shield may be sacrificial and/or abradable. In this arrangement the component 60, the light source 108 and the supply nozzle 130 also remain in fixed positions relative to each other during the drilling and viewing of each slot. The camera 114 also remains in a fixed position relative to the component 60, the light source 108 and the supply nozzle 130.

The advantage of this embodiment of the present disclosure is that it enables in process inspection of milling, or grinding, machines or milling, or grinding, processes using back lighting. The present disclosure allows the light source to remain static in the path of the milling, or grinding, tool and avoids the need for complex mechanisms to move the light source into and out of the path of the milling, or grinding, tool. The present disclosure ensures that the lighting, lumen, level remains substantially constant and enables comparative measurements to be made. The present disclosure reduces, or prevents, the material particles, dust, machining swarf produced by the milling, or grinding, tool cutting through the component collecting, e.g. depositing or settling, on the light source and hence prevents, or reduces, the light output from the light source reducing and thus makes the comparative measurements easier.

The present disclosure may also be applicable to machining fir-tree shaped slots in a high-pressure turbine disc, it may also be applicable to machining fir-tree shaped slots in intermediate-pressure turbine discs, low-pressure turbine discs or compressor discs and may also be applicable to dovetail or other shaped slots in turbine discs or compressor discs.

Although the present disclosure has been described with reference to blade retention slots in the rim of a turbine disc, or a compressor disc, it is equally applicable to slots in other component and/or slots for other purposes. The slots may be part-circular, elliptical, race-track shape or any other suitable shape in cross-section. The slots may be arranged perpendicularly to the side/surface of the component or may be arranged at an angle to the side/surface of the component.

Although the present disclosure has referred to drilling, milling and grinding it may also be applicable to other machining processes in which the tool machines through the component from a first side of the component to a second side of the component to form a shape, or profile, through the component.

The path of the tool is the direction of travel of the laser beam or the direction of travel of the tool relative to the component.

Although the present disclosure has referred to the use of a gas source and flowing gas over the light source it may be equally possible to use a fluid source and flow fluid over the light source.

In each of the embodiments described above it is also possible to provide a fluid collector to collect the fluid after it has passed over the surface of the light source. Ideally the fluid collector and the fluid source are positioned on opposite sides of the light source. The fluid collector may comprise a collector nozzle to collect the fluid after it has passed over the surface of the light source. The collector nozzle may be positioned adjacent to the light source. The collector nozzle may have an elongate inlet to collect a sheet of fluid after it has passed over the surface of the light source. The fluid collector may comprise a pump connected to the collector nozzle to suck the fluid into the collector nozzle and away from the light source. Alternatively, in each of the embodiments described above it is also possible to only provide a fluid collector and the fluid collector may comprise a pump connected to the collector nozzle to suck the fluid into the collector nozzle and hence across, over, the light source. The advantage of the fluid collector is that it also collects dross, dust, spatter produced by laser drilling and prevents it resettling on previously drilled cooling holes and internal surfaces of the machine and prevents it becoming a health hazard to the machine operators. Similarly, the fluid collector also collects the material particles, dust, machining swarf produced by the milling, or grinding, process, with similar benefits. Thus, the present disclosure provides a device to produce/provide a flow of fluid over, across, the surface of the light source.

It is to be noted that in all the embodiments of the present disclosure that the tool is positioned at one side of the component and the light source and the supply nozzle and/or the collector nozzle are positioned at the opposite side of the component. It is to be noted that in all the embodiments of the present disclosure that the component, the light source and the supply nozzle and/or the collector nozzle remain in fixed positions relative to each other during the machining and viewing of each shape.

Although the present disclosure has been described with reference to a turbofan gas turbine engine it is equally applicable to a turbojet gas turbine engine, a turbo-shaft gas turbine engine or a turbo-propeller gas turbine engine.

Although the present disclosure has been described with reference to a three shaft gas turbine engine it is equally applicable to a two shaft gas turbine engine or a single shaft gas turbine engine.

Although the present disclosure has been described with reference to an aero gas turbine engine it is equally applicable to a marine gas turbine engine, an industrial gas turbine engine or an automotive gas turbine engine and is equally applicable to other types of turbomachine and steam turbines etc.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

The invention claimed is:

1. An apparatus for machining and inspecting a shape through a component comprising:
a tool;
a light source positioned in a path of the tool, the light source remaining static in the path of the tool;
a camera positioned or positionable at a location with a line of sight view of the light source through the machined shape through the component, the tool and the camera being positioned at a first side of the component;
a processor configured to:
measure parameters of the machined shape through the component using a view of the machined shape provided by the camera, and
compare the measured parameters of the machined shape through the component with required parameters for the machined shape through the component; and
a device configured to provide a flow of fluid over a surface of the light source, the device and the light source being positioned at an opposite side of the component relative to the position of the tool and the camera, the device being selected from a group consisting of: a supply nozzle to blow the fluid over the surface of the light source, and a collector nozzle to suck the fluid over the surface of the light source, wherein
the component, the light source, and the device remain in fixed positions relative to each other during the machining and the inspecting of the machined shape through the component.

2. The apparatus as claimed in claim 1, wherein the light source is one of: a light bulb, a light emitting diode (LED), a fluorescent tube, a panel comprising a plurality of LEDs and a diffusing reflector and a light source.

3. The apparatus as claimed in claim 1, wherein the device includes a pump to provide the flow of fluid over the surface of the light source.

4. The apparatus as claimed in claim 1, wherein the supply nozzle is positioned adjacent to the light source.

5. The apparatus as claimed in claim 1, wherein the supply nozzle has an elongate outlet to provide a sheet of fluid over the light source.

6. The apparatus as claimed in claim 1, wherein the collector nozzle is positioned adjacent to the light source.

7. The apparatus as claimed in claim 1, wherein the collector nozzle has an elongate inlet to collect a sheet of fluid after the fluid has passed over the surface of the light source.

8. The apparatus as claimed in claim 1, wherein the collector nozzle and the supply nozzle are positioned on opposite sides of the light source.

9. The apparatus as claimed in claim 1, wherein a transparent shield is provided to protect the light source.

10. The apparatus as claimed in claim 9, wherein the transparent shield is selected from a group consisting of: a sacrificial transparent shield, and an abradable transparent shield.

11. The apparatus as claimed in claim 9, wherein the transparent shield is provided between the light source and the flow of fluid, or the flow of fluid is provided between the light source and the transparent shield.

12. The apparatus as claimed in claim 9, wherein the transparent shield is selected from a group consisting of: a sheet of glass and a sheet of polymeric material.

13. The apparatus as claimed in claim 1, wherein the tool is selected from a group consisting of: a laser source to laser machine a shape through the component, a drilling bit to drill a hole through the component, an EDM electrode to drill a hole through the component, a milling tool to mill a slot through the component, and a grinding tool to grind a slot through the component.

14. A computer-implemented method of machining and inspecting a shape through a component comprising:
providing a tool at a first side of the component;
positioning a light source in a path of the tool at a second and opposite side of the component, the light source remaining static in the path of the tool;
providing a camera at the first side of the component;
providing a device to provide a flow of fluid over a surface of the light source at the second side of the component;
illuminating the second side of the component at least in a vicinity of the path of the tool;
flowing the fluid over the surface of the light source to protect the light source;
machining through the component from the first side of the component to the second side of the component to form the shape through the component;
positioning the camera at a location with a line of sight view of the light source through the machined shape through the component;
viewing the machined shape through the component using the illumination provided by the light source at the second side of the component;
measuring parameters, by a processor, of the machined shape through the component using a view of the machined component provided by the camera;
comparing the measured parameters, by the processor, of the machined shape through the component with required parameters for the machined shape through the component; and
blowing the fluid over the surface of the light source and/or sucking the fluid over the surface of the light source, wherein
the component, the light source, and the device remain in fixed positions relative to each other during the machining and the inspecting of the machined shape through the component.

15. The computer-implemented method as claimed in claim 14, further comprising positioning a supply nozzle adjacent to the light source and supplying the fluid from the supply nozzle.

16. The computer-implemented method as claimed in claim 15, wherein the supply nozzle has an elongate outlet and provides a sheet of fluid over the light source.

17. The computer-implemented method as claimed in claim 14, further comprising positioning a collector nozzle adjacent to the light source and collecting the fluid using the collector nozzle.

18. The computer-implemented method as claimed in claim 17, wherein the collector nozzle has an elongate inlet and collects a sheet of fluid after the fluid has passed over the surface of the light source.

19. The computer-implemented method as claimed in claim 14, further comprising positioning a collector nozzle and a supply nozzle on opposite sides of the light source.

20. The computer-implemented method as claimed in claim 14, further comprising supplying a gas over the light source.

21. The computer-implemented method as claimed in claim 20, wherein the gas is selected from a group consisting of: air, nitrogen, and an inert gas.

22. The computer-implemented method as claimed in claim 14, further comprising providing a laser source and laser machining the shape through the component.

23. The computer-implemented method as claimed in claim 22, further comprising laser drilling a hole through the component.

24. The computer-implemented method as claimed in claim 22, further comprising:
   providing the camera with a permanent line of sight view of the light source through the laser machined shape;
   providing an optical switch in a path of a laser beam from the laser source; and
   switching the optical switch between a first position for supplying the laser beam there-through to laser machine the shape through the component and a second position for allowing the camera to view the laser machined shape.

25. The computer-implemented method as claimed in claim 22, further comprising:
   providing the camera with a temporary line of sight view of the light source through the laser machined shape; and
   moving the camera between a first position in which the camera is not in the optical path of the laser beam to allow the laser beam to laser machine the shape through the component and a second position in which the camera is in the optical path of the laser beam for allowing the camera to view the laser machined shape.

26. The computer-implemented method as claimed in claim 22, further comprising re-drilling a laser drilled hole in the component when the measured parameters do not satisfy at least one of the required parameters for the laser drilled hole, or terminating the laser drilling of the hole when the measured parameters of the laser drilled hole satisfy the required parameters.

27. The computer-implemented method as claimed in claim 14, wherein a step of the method is selected from a group consisting of: providing a drilling bit and drilling a hole through the component, and providing an EDM electrode and drilling a hole through the component.

28. The computer-implemented method as claimed in claim 14, further comprising drilling a hole through the component selected from a group consisting of: a combustion chamber wall, a combustion chamber tile, a combustion chamber segment, a combustion chamber heat shield, a turbine blade, and a turbine vane.

29. The computer-implemented method as claimed in claim 14, wherein a step of the method is selected from a group consisting of: providing a milling tool and milling a slot through the component, and providing a grinding tool and grinding a slot through the component.

30. The computer-implemented method as claimed in claim 29, wherein the grinding tool is a fir-tree shaped grinding tool and the component is selected from a group consisting of: a turbine disc and a compressor disc.

\* \* \* \* \*